US009913598B2

United States Patent
Landau et al.

(10) Patent No.: US 9,913,598 B2
(45) Date of Patent: Mar. 13, 2018

(54) NONINVASIVE NONDISRUPTIVE ASSESSMENT OF EYELID DYNAMICS BY MEANS OF EDDY-CURRENT NO-TOUCH SENSORS

(71) Applicant: Igor Landau, Palo Alto, CA (US)

(72) Inventors: Alexander Landau, Boulder, CO (US); Igor Landau, Palo Alto, CA (US)

(*) Notice: Subject to any disclaimer, the term of this patent is extended or adjusted under 35 U.S.C. 154(b) by 61 days.

(21) Appl. No.: 14/886,045

(22) Filed: Oct. 17, 2015

(65) Prior Publication Data

US 2017/0105660 A1   Apr. 20, 2017

(51) Int. Cl.
| | | |
|---|---|---|
| G08B 23/00 | (2006.01) |
| A61B 5/11 | (2006.01) |
| A61B 3/113 | (2006.01) |
| A61B 5/00 | (2006.01) |
| A61B 3/10 | (2006.01) |

(52) U.S. Cl.
CPC .............. *A61B 5/1103* (2013.01); *A61B 3/10* (2013.01); *A61B 3/113* (2013.01); *A61B 5/4082* (2013.01); *A61B 5/6803* (2013.01); *A61B 2562/0257* (2013.01)

(58) Field of Classification Search
None
See application file for complete search history.

(56) References Cited

U.S. PATENT DOCUMENTS

| | | | |
|---|---|---|---|
| 6,878,554 B1* | 4/2005 | Schermer ............. | B01J 19/0046 422/521 |
| 2006/0135880 A1* | 6/2006 | Sarkela .................. | A61B 5/048 600/544 |
| 2012/0229248 A1* | 9/2012 | Parshionikar .......... | G08B 21/06 340/3.1 |

* cited by examiner

Primary Examiner — Brian Zimmerman
Assistant Examiner — Kevin Lau

(57) ABSTRACT

Systems and processes for measurement of the eyelid movements of a subject, which explores eyelids' electrical conductivity, namely the established fact that eyelids are acting as sliding electrodes moving over the cornea, is comprised of a system for generating a high frequency weak and harmless oscillating electromagnetic field in the proximity of the eyelid movement path without interference with the vision or activity of any such subject, therefore induces so-called Eddy Currents in the eyelid, which in its turn produce its own electromagnetic field with a value depended on the eyelid position; the interaction between the basic oscillating electromagnetic field and the field generated by the eyelid is changing electromagnetic field inductance, which will be measured with very high accuracy by means of resonance sensing electronics; such systems can transmit data from its detecting electronics to a remote monitor that compels no restrictions on operator activity.

2 Claims, 3 Drawing Sheets

NONINVASIVE NONDISRUPTIVE ASSESSMENT OF EYELID DYNAMICS BY MEANS OF EDDY-CURRENT NO-TOUCH SENSORS

This invention was made with government support under grant No IIP-1448564 awarded by National Sciences Foundation (NSF). The government has certain rights in the invention.

This invention claims the benefit of priority of U.S. Provisional Patent Application Ser. No. 62/065,634 filed Oct. 18, 2014.

FIELD OF THE INVENTION

The present invention is in the technical field of eyeblinks measurements. More particularly, the present invention describes novel nonintrusive technology for direct precise assessment of eyelid displacement in time by means of electromagnetic capacitive-inductive sensing.

DESCRIPTION OF THE PRIOR ART

Importance of Assessment of Eyeblinks

Eye blink assessment has a wide range of applications from detection of operator fatigue, for use in human computer interaction, and as control input modality for people with disabilities to be able to interact with computers, mobile phones, and patient assistance devices.

Health Care Applications

It has been established that dopamine activity correlates directly with blink rate. That is why eye blink rate is considered a potential noninvasive marker of central dopamine activity. Blink rate was utilized in a series of clinical studies of Parkinson's disease (PD), Huntington's disease, dystonia and schizophrenia. Asymmetric blinking could be a sign of facial nerve palsy, myasthenia gravis, or other pathology.

Vigilance Control

Eyelid movement traits are highly informative in determining vigilance state and level of cognitive alertness critical for operator task activity requiring sustained performance under monotonous conditions (e.g. driving). Operator fatigue is one of the main factors that can impact the ability of pilots, air traffic controllers, cyber operators, Transportation Security Administration (TSA)—inspectors, unmanned aerial systems pilots, and truck drivers, all of whom must maintain their performance over time.

Subjective estimates of sleepiness are unreliable. Experiments have demonstrated that subjects cannot reliably predict when they are impaired to the point of having vigilance lapses, which can lead to so-called microsleeps. Microsleeps are temporary episode of light sleep which may last for fractions of a second or up to twenty seconds wherein an individual fails to respond to sensory inputs and becomes severely degraded, even leading to accidents.

Drivers, for example, often recognize when they are experiencing sleepiness, but they do not always translate those introspections into accurate detection when their level of drowsiness will decrease to the point of danger and they are missing signals, or when they will have an uncontrolled sleep onset while driving.

Even a fraction of a second delay in alerting the driver can potentially be fatal. The device needs to be able to alert the driver before that. Technology may offer the potential for an earlier and more reliable warning of performance-impairing sleepiness, before drowsiness leads to a catastrophic outcome.

It has been well-established that the early dynamic changes in eye blinks, particularly the speed and frequency of the eyelids closing and reopening, provide a reliable and direct physiological marker of vigilance and alertness. Present methods for recording eye blinks can be summarized in general as:
Video-facial monitoring techniques;
devices using eye reflections;
devices for acquiring and analyzing an accurate blink electromyogram (EMG)

A plethora of published patents describe multiple variations of the above mentioned approaches, so here we briefly depict these methods together with some exemplary patents associated with each.

Video-facial monitoring technique (U.S. Pat. No. 5,933,527 A) involves a combination of infrared light directed at the eye and the reflection of this light of the eye retina is then captured by a video camera(s) together with special eye tracking software, which are then processed and converted into measures of eyelid closure in near real time.

However such techniques generally do not work well in daylight, because ambient sunlight causes a person's eye pupils to "stop down" and therefore makes for a smaller pupil entry point from which to obtain retinal reflections. It is important to note also that the 60 Hz sampling rate characteristic of standard video-monitoring hardware is insufficient for high-resolution measurement of eyelid dynamics. Utilization of high-speed cameras dramatically increases the expense (by several thousand dollars) of needed hardware that makes it less affordable for field applications.

Devices using reflection (U.S. Pat. No. 5,933,527 A) light emitting diodes (LEDs) mounted on an eyeglass frame shine infra-red light toward the eye and a photosensitive device responds to the light reflected from the eye.

Devices using electromyogram (EMG) (U.S. Pat. No. 7,639,146 B2) use electrodes to be positioned over one or more muscles of one or both eyes, where the muscles are known to assist in closing the eyelids. The electrodes detect electrical current in the muscle(s) and transmit signal(s) representative of the electrical current to a signal processing device.

In general, all methods mentioned above require eye video-tracking system, or intrusive elements that have limited user acceptance by the equipment operators. Accordingly, today, non-intrusive, reliable, high-resolution assessments of eyelid dynamics are still inadequate for use as an oculomotor-based fatigue assessment technology. Our proposed patented system would fill that technological gap.

SUMMARY OF THE INVENTION

The systems and processes of the present invention provide dynamic eyelid measurements. The systems and processes of the present invention avoid and overcome the disadvantages of the prior art by the utilization of the conductive properties of the eyelids of a subject to provide dynamic measurements movement assessment of the eyelids.

This is due to the fact that eyelid is a conductor because of a rich supply of capillary blood vessels in the eyelid tissue. As a result, during a movement, such as blinking or closing process, an eyelid acts as a sliding electrode moving along the curved surface of the cornea.

Using this natural characteristic of the eyelid, the systems and processes of the present invention explores the eyelid's electrical conductivity for practical measurements. In preferred embodiments this is done by generating a weak, completely harmless radio frequency oscillating electromagnetic field in the proximity of the eyelid movement path.

The process of movement of the eyelid in such an oscillating electromagnetic field is susceptible to measurement and recording with very high accuracy, for by employing inductive-capacitive (Eddy-current) proximity sensors that are capable of high resolution measurements of position and displacement.

Such sensors operate with electromagnetic fields. To generate electromagnetic fields, a high-frequency driver amplifier is connected to a wire-wrapped, air-core coil in parallel electrical configuration with a capacitor and forms a LC-resonator. The values of the parallel inductor (L) and capacitor (C) define the circuit resonate frequency according to:

$$F_{Resonance\ Frequency}(Hz) = \frac{1}{2\pi\sqrt{LC}}$$

A driver could be a High Performance Phase Lock Loop (PLL) that ensures a precise detection in the change of sensor resonance circuit frequency induced by eyelid movement.

Resonant circuit radiates electromagnetic field. The radiated electromagnetic field induces small electrical currents in the eyelid. These small electrical currents are called eddy currents. The generation of small time-varying electrical currents in an eyelid results in a time-varying electromagnetic field that is radiated externally to the resonant circuit, in opposition to the sensor's electromagnetic field. The result of the interaction changes the apparent resonant circuit impedance that this is the basis for determining eyelid-to-coil position information.

The interaction between the opposing electromagnetic fields depends on how far away the eyelid is from the circuit.

The miniature sensor could be worn for a day-long assessment for wireless transmission of eyelid movement data in any environment without interfering with a person's everyday activities.

In preferred embodiments of the present invention, the air-core coil may be composed of several turns of coated wire, or it could be printed on a printed circuit board and clipped to an eyeglasses frame (or to a frame resembling eyeglasses if a person does not wear eyeglasses) for placement proximate an eye and eyelid.

In another implementation of the present invention, insulated wire in a form of, an air core may be embedded inside a contact lens. Such a contact lens implementation would best include the presence of a miniature microchip circuit in the contact lens to generate electromagnetic field, and to process the resultant data and to potentially communicate it via near field communication protocols to, for example, a mobile device such as a smart phone or a smart watch or a wrist band.

This measurement provides a high-resolution, inexpensive direct, non-intrusive assessment of eyelid movements that does not interfere with a person's everyday activity.
Experimental Realization of Electromagnetic Induction Concept The following section describes realization of described above technology with use commercial off-the-shelf Inductance-to-Digital Micro-Converter, LDC1000 (Texas Instruments), which has allowed the electronics to be assembled on lightweight eyeglass frames. The study has demonstrated high accuracy in non-intrusive detection of eye blinks that was previously unavailable for fatigue detection systems.

Testing on 15 subjects has confirmed that eyelid movements can be measured and recorded by employing advanced resonance sensing electronics in the environment of an oscillating weak and harmless electromagnetic field.

BRIEF DESCRIPTION OF THE DRAWINGS

The accompanying drawings illustrate complete preferred embodiments of the present invention, by way of example only, according to the best modes presently devised for the practical application of the principles thereof, and in which.

DETAILED DESCRIPTION OF THE DRAWINGS

Figure 1:
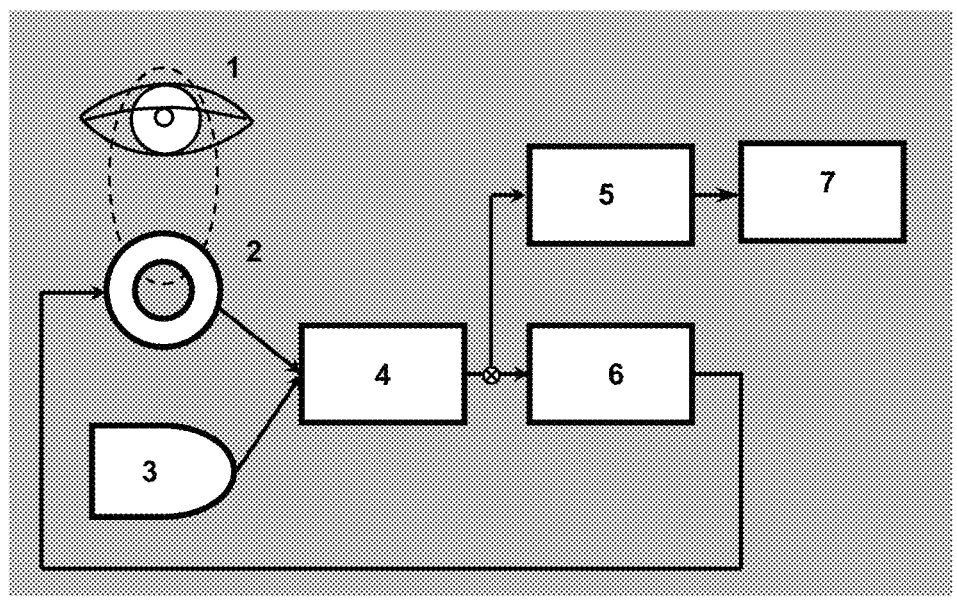
FIG. 1 schematically illustrates the elements for measuring eyelid dynamics, according to one preferred embodiment of the present invention, in a High Performance Phase Lock Loop (PLL), as explained below.
Figure 2:
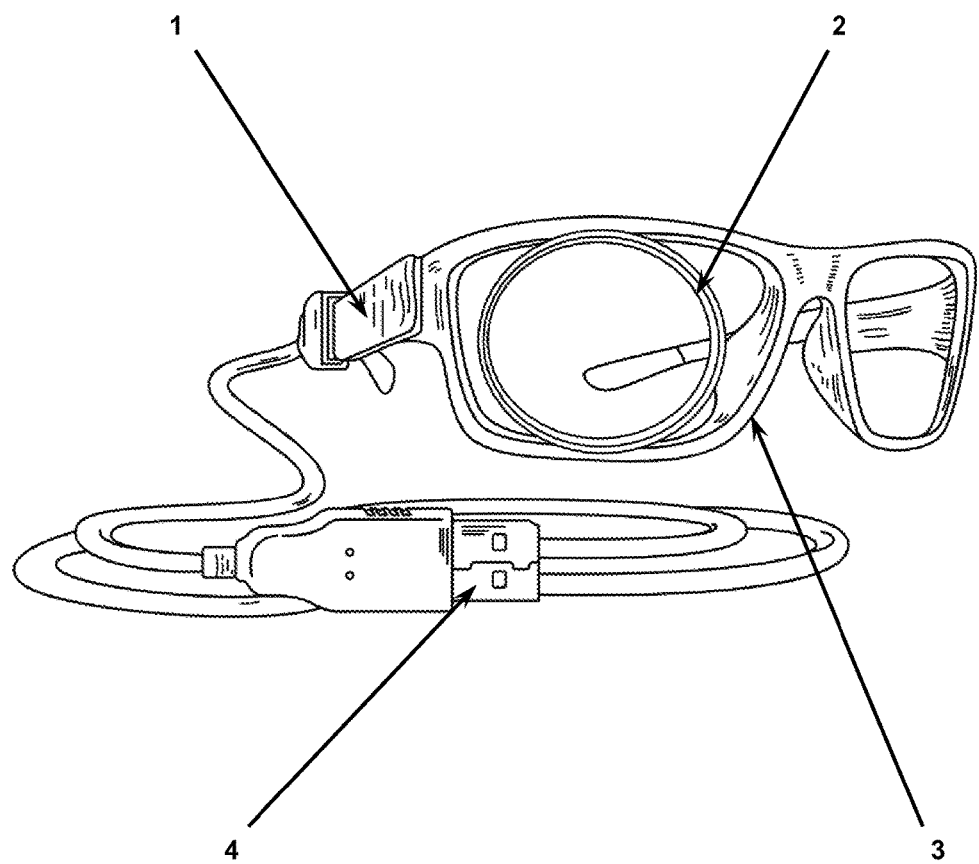
FIG. 2 is a photograph illustrating an air-core coil with Inductance-to-Digital Micro-Converter LDC1000, of the present invention, carried for convenience on an eyeglass frame used in the experimental study.

The elements for measuring eyelid dynamics, according to one preferred embodiment of the present invention is schematically illustrated in FIG. 1. It shows a combined eye with an eyelid (1), which provides the environment for measuring eyelid dynamics according to the systems and processes of the present invention. LC resonator (2), (for example in the form of an air core carried on an eyeglass frame, as shown in FIG. 2), is designed to placed and held in the proximity of eye/eyelid (1). Cristal Oscillator with short term frequency stability. In preferred embodiments of the present invention, changes in frequency detected by the air core are processed through Phase Detector (4), Amplifier (5) and to Loop Filter (6), for transmission to, or recording by, or display by other systems (7).

It will be appreciated that the Electronic Circuit of FIG. 1 is, in fact, a Phase Locked Loop (PLL) that ensures a precise detection in the change of sensor resonance circuit frequency induced in the air core by proximate eyelid movement.

Figure 3:
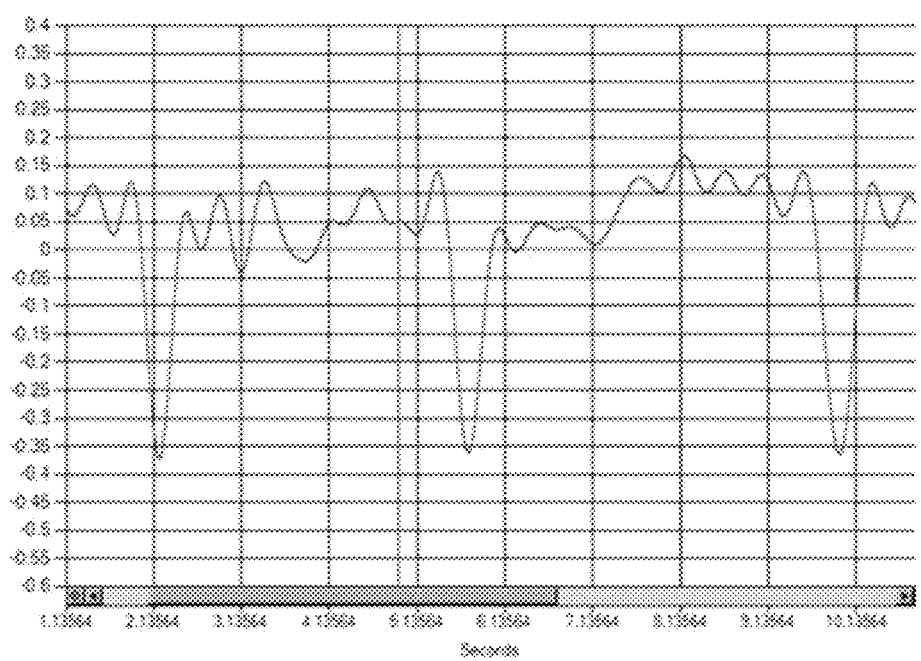
FIG. 3 presents a computer display graphically showing measurement results of three eye blinks with about 2 second intervals as determined by the eyelid dynamic measuring systems and processes of the present.

On FIG. 2 shows, in addition to the frame (3) and LC-resonator (2), Inductance-to-Digital Micro-Converter (1), such as a tiny commercial off-the-shelf Inductance-to-Digital Micro-Converter, LDC1000 (Texas Instruments), in operative connection with LC-resonator (2), assembled on eyeglass frame (3) with USB connector (4) to a computer On FIG. 3 has shown an image of computer displays inductance measurement of three eye blinks profiles on amplified time scale with about 2 sec. interval of a person during a test.

While the invention has been particularly shown, described and illustrated in detail with reference to preferred embodiments, processes, and modifications thereof, it should be understood by those skilled in the art that the foregoing and other modifications are exemplary only, and that equivalent changes in form and detail may be made therein without departing from the true spirit and scope of the invention as claimed, except as precluded by the prior art.

What we claim is:

1. A system for precise measurement of eyelid dynamics clipped to an eyeglass frame, comprising: a voltage controlled oscillator formed by several turns of coated thin wire attached to the eyeglass frame and a locked to crystal oscillator to create a high frequency axis symmetrical electromagnetic field along an eyelid path along a cornea of a user; a high performance Phase Lock Loop (Phase Detector) and a nonlinear high-order Loop filter to detect change of a resonance counter frequency as a result of changes with the nonlinear high-order Loop filter equivalent capacitance from the detected motion of a user's eyelid, and an amplifier to amplify the generated output signal of the Phase Detector.

2. The system of claim 1, which could be implemented by commercial off-the-shelf Inductance-to-Digital Micro-Converter microchip assembled on eyeglass frame with wireless or USB connector to a computer for processing of the data.

* * * * *